United States Patent
Xie et al.

(10) Patent No.: US 10,272,423 B2
(45) Date of Patent: Apr. 30, 2019

(54) PROCESSES USING MOLECULAR SIEVE SSZ-105

(71) Applicant: Chevron U.S.A. Inc., San Ramon, CA (US)

(72) Inventors: Dan Xie, Richmond, CA (US); Christopher Michael Lew, Richmond, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 316 days.

(21) Appl. No.: 15/276,890

(22) Filed: Sep. 27, 2016

(65) Prior Publication Data

US 2017/0106357 A1    Apr. 20, 2017

Related U.S. Application Data

(60) Provisional application No. 62/242,352, filed on Oct. 16, 2015.

(51) Int. Cl.
*B01D 53/02* (2006.01)
*C07C 1/20* (2006.01)
(Continued)

(52) U.S. Cl.
CPC ............ *B01J 29/80* (2013.01); *B01D 53/02* (2013.01); *B01D 53/229* (2013.01); *B01J 20/18* (2013.01); *B01J 29/068* (2013.01); *B01J 29/072* (2013.01); *B01J 29/56* (2013.01); *B01J 29/763* (2013.01); *C07C 1/20* (2013.01); *C07C 209/16* (2013.01); *C07C 209/68* (2013.01); *C10G 3/49* (2013.01); *B01D 53/228* (2013.01); *B01D 53/9413* (2013.01); *B01D 2253/1085* (2013.01); *B01D 2253/311* (2013.01); *B01D 2255/2092* (2013.01); *B01D 2255/30* (2013.01); *B01D 2255/91* (2013.01); *B01D 2256/24* (2013.01); *B01D 2257/504* (2013.01); *B01D 2257/702* (2013.01); *C07C 2529/50* (2013.01); *C07C 2529/70* (2013.01); *C07C 2529/80* (2013.01); *C10G 2400/20* (2013.01);
(Continued)

(58) Field of Classification Search
None
See application file for complete search history.

(56) References Cited

U.S. PATENT DOCUMENTS 4,568,654 A * 2/1986 Valyocsik ................ B01J 29/70
                                                         423/332

FOREIGN PATENT DOCUMENTS

WO    WO2013035054    * 3/2013

OTHER PUBLICATIONS

M.M.J. Treacy, J.M. Newsam and M.W. Deem "A general recursion method for calculating diffracted intensities from crystals containing planar faults" Proc. R. Soc. Lond. A 1991, 433, 499-520.
(Continued)

*Primary Examiner* — Colleen P Dunn
(74) *Attorney, Agent, or Firm* — Terrence M. Flaherty

(57) ABSTRACT

Uses for a new crystalline molecular sieve designated SSZ-105 are disclosed. SSZ-105 is synthesized using N,N-dimethylpiperidinium cations as a structure directing agent. SSZ-105 is a disordered aluminosilicate molecular sieve comprising at least one intergrown phase of an ERI framework type molecular sieve and an LEV framework type molecular sieve.

15 Claims, 11 Drawing Sheets

(51) Int. Cl.
- *C07C 209/16* (2006.01)
- *B01J 29/80* (2006.01)
- *B01J 20/18* (2006.01)
- *C07C 209/68* (2006.01)
- *B01D 53/22* (2006.01)
- *C10G 3/00* (2006.01)
- *B01J 29/068* (2006.01)
- *B01J 29/072* (2006.01)
- *B01J 29/56* (2006.01)
- *B01J 29/76* (2006.01)
- *B01D 53/94* (2006.01)

(52) U.S. Cl.
CPC ............... *Y02C 10/08* (2013.01); *Y02C 10/10* (2013.01); *Y02P 20/152* (2015.11); *Y02P 20/52* (2015.11); *Y02P 30/42* (2015.11)

(56) References Cited

OTHER PUBLICATIONS

R. Szostak "Molecular Sieves Principles of Synthesis and Identification" Second Edition, Blackie Academic & Professional, London, 62-76 (1998).

\* cited by examiner

PROCESSES USING MOLECULAR SIEVE SSZ-105

TECHNICAL FIELD

This disclosure relates to a new crystalline molecular sieve designated SSZ-105, a method for preparing SSZ-105, and uses for SSZ-105. SSZ-105 is a disordered aluminosilicate molecular sieve comprising at least one intergrown phase of an ERI framework type molecular sieve and an LEV framework type molecular sieve.

BACKGROUND

Molecular sieve materials, both natural and synthetic, have been demonstrated in the past to be useful as adsorbents and to have catalytic properties for various types of organic conversion reactions. Certain molecular sieves, such as zeolites, aluminophosphates, and mesoporous materials, are ordered, porous crystalline materials having a definite crystalline structure as determined by X-ray diffraction. Within the crystalline molecular sieve material there are a large number of cavities which may be interconnected by a number of channels or pores. These cavities and pores are uniform in size within a specific molecular sieve material. Because the dimensions of these pores are such as to accept for adsorption molecules of certain dimensions while rejecting those of larger dimensions, these materials have come to be known as "molecular sieves" and are utilized in a variety of industrial processes.

Although many different crystalline molecular sieves have been discovered, there is a continuing need for new molecular sieves with desirable properties for gas separation and drying, organic conversion reactions, and other applications. New molecular sieves can contain novel internal pore architectures, providing enhanced selectivities in these processes.

Molecular sieves are classified by the Structure Commission of the International Zeolite Association according to the rules of the IUPAC Commission on Zeolite Nomenclature. According to this classification, framework type zeolites and other crystalline microporous molecular sieves, for which a structure has been established, are assigned a three letter code and are described in the "*Atlas of Zeolite Framework Types*," Sixth Revised Edition, Elsevier, 2007.

Molecular sieves may be ordered or disordered. Ordered molecular sieves are built from structurally invariant building units, called Period Building Units (PerBUs), and are periodically ordered in three dimensions. Crystal structures built from PerBUs are called end-member structures if periodic ordering is achieved in all three dimensions. Disordered structures, on the other hand, show periodic ordering in less than three dimensions. One such disordered structure is a disordered planar intergrowth in which the building units from more than one framework type are present. Such intergrowths frequently have significantly different catalytic properties from their end members. For example, zeolite ZSM-34 is well known intergrowth of ERI and OFF framework types and exhibits a methanol-to-olefins performance superior to that of its individual component materials.

Disclosed herein is a unique disordered aluminosilicate molecular sieve designated SSZ-105 which comprises at least one intergrown phase of an ERI framework type molecular sieve and an LEV framework type molecular sieve.

SUMMARY

The present disclosure is directed to a new family of crystalline molecular sieves with unique properties, referred to herein as "molecular sieve SSZ-105" or simply "SSZ-105." Molecular sieve SSZ-105 comprises at least one intergrown phase of an ERI framework type molecular sieve and an LEV framework type molecular sieve.

In its calcined form, molecular sieve SSZ-105 has a chemical composition, in terms of mole ratios, comprising the following:

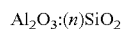
$Al_2O_3$:$(n)SiO_2$ wherein n has a value from 10 to 50.

In one aspect, there is provided a process for preparing molecular sieve SSZ-105 by (a) preparing a reaction mixture containing: (1) at least one source of silicon oxide; (2) at least one source of aluminum oxide; (3) at least one source of a Group 1 metal (M), wherein M is selected from the group consisting of potassium and combinations of sodium and potassium; (4) hydroxide ions; (5) N,N-dimethylpiperidinium cations; and (6) water; and (b) subjecting the reaction mixture to crystallization conditions sufficient to form crystals of the molecular sieve.

In its as-synthesized and anhydrous form, molecular sieve SSZ-105 has a chemical composition, in terms of mole ratios, comprising the following:

|  | Broad | Exemplary |
| --- | --- | --- |
| $SiO_2/Al_2O_3$ | 10 to 50 | 15 to 40 |
| $Q/SiO_2$ | 0.02 to 0.20 | 0.05 to 0.20 |
| $M/SiO_2$ | 0.01 to 0.20 | 0.02 to 0.15 | wherein Q comprises N,N-dimethylpiperidinium cations and M is a Group 1 metal selected from the group consisting of potassium and combinations of sodium and potassium.

Additionally, the molecular sieve disclosed herein is useful in a wide range of processes, including separation processes and as a catalyst in organic conversion reactions. In further aspect, there is disclosed a process for converting a feedstock comprising an organic compound to a conversion product which comprises the step of contacting the feedstock with a catalyst at organic compound conversion conditions, the catalyst comprising an active form of the molecular sieve described herein.

DETAILED DESCRIPTION

Introduction

Figure 1:
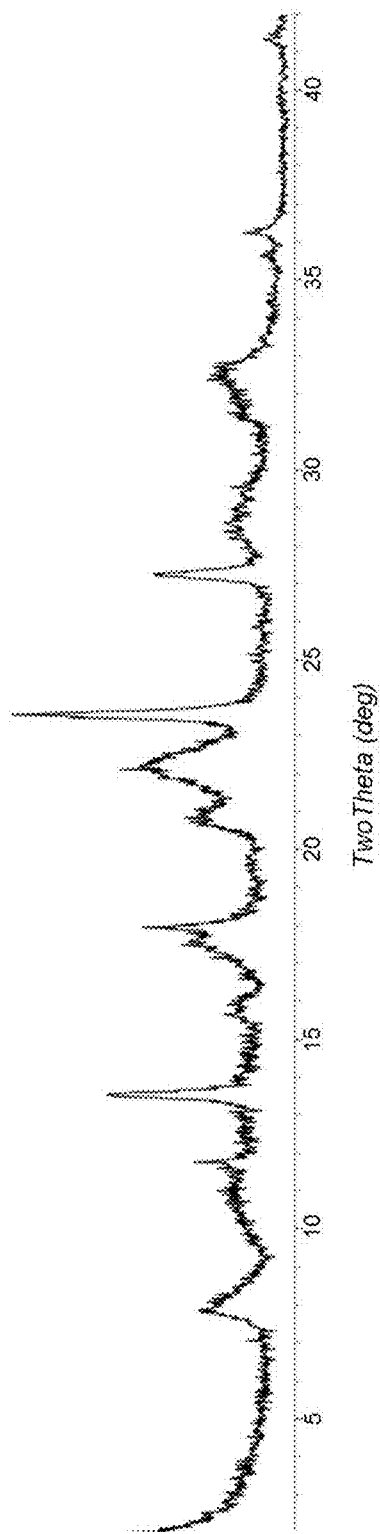
FIG. 1 is a powder X-ray diffraction (XRD) pattern of the as-synthesized molecular sieve prepared in Example 1.

The following terms will be used throughout the specification and will have the following meanings unless otherwise indicated.

The term "framework type" is used in the sense described in the "*Atlas of Zeolite Framework Types*," Sixth Revised Edition, Elsevier, 2007.

As used herein, the numbering scheme for the Periodic Table Groups is as disclosed in *Chem. Eng. News,* 63(5), 26-27 (1985).

Intergrown molecular sieve phases are disordered planar intergrowths of molecular sieve frameworks. Reference is directed to the "Catalog of Disordered Zeolite Structures," 2000 Edition, published by the Structure Commission of the International Zeolite Association and to the "*Collection of Simulated XRD Powder Patterns for Zeolites*," Fifth Revised Edition, Elsevier, 2007, published on behalf of the Structure Commission of the International Zeolite Association for a detailed explanation on intergrown molecular sieve phases.

The molecular sieves described herein are disordered planar intergrowths of end-member structures ERI and LEV. Both of these two framework types belong to the group that has double 6-rings (d6r) as secondary building units. Intergrown ERI/LEV molecular sieves comprise regions of ERI framework type sequences and regions of LEV framework type sequences. Each change from an ERI to an LEV framework type sequence results in a stacking fault.

In preparing molecular sieve SSZ-105, an N,N-dimethylpiperidinium cation is used as a structure directing agent ("SDA"), also known as a crystallization template. The SDA useful for making SSZ-105 has the following structure (1):

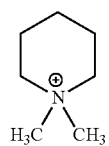

(1)

N,N-dimethylpiperidinium cation

The SDA cation is associated with anions which may be any anion that is not detrimental to the formation of SSZ-105. Representative anions include elements from Group 17 of the Periodic Table (e.g., fluoride, chloride, bromide and iodide), hydroxide, sulfate, tetrafluoroboroate, acetate, carboxylate, and the like.

Reaction Mixture

In general, molecular sieve SSZ-105 is prepared by: (a) preparing a reaction mixture containing (1) at least one source of silicon oxide; (2) at least one source of aluminum oxide; (3) at least one source of a Group 1 metal (M), wherein M is selected from the group consisting of potassium and combinations of sodium and potassium; (4) hydroxide ions; (5) N,N-dimethylpiperidinium cations; and (6) water; and (b) subjecting the reaction mixture to crystallization conditions sufficient to form crystals of the molecular sieve.

The composition of the reaction mixture from which the molecular sieve is formed, in terms of mole ratios, is identified in Table 1 below:

TABLE 1

| Components | Broad | Exemplary |
|---|---|---|
| $SiO_2/Al_2O_3$ | 10 to 100 | 15 to 80 |
| $M/SiO_2$ | 0.05 to 1.00 | 0.10 to 0.30 |
| $Q/SiO_2$ | 0.05 to 0.70 | 0.20 to 0.45 |
| $OH/SiO_2$ | 0.10 to 1.00 | 0.30 to 0.80 |
| $H_2O/SiO_2$ | 10 to 100 | 15 to 60 | wherein compositional variables M and Q are as described herein above.

Sources useful herein for silicon oxide include fumed silica, precipitated silicates, silica hydrogel, silicic acid, colloidal silica, tetra-alkyl orthosilicates (e.g., tetraethyl orthosilicate), and silica hydroxides.

Sources useful herein for aluminum oxide include aluminates, alumina, and aluminum compounds (e.g., aluminum chloride, aluminum hydroxide, and aluminum sulfate), kaolin clays, and other zeolites (e.g., zeolite Y).

In the present synthesis method, the Group 1 metal (M) is selected from the group consisting of potassium and combinations of sodium and potassium. The sodium source may be sodium hydroxide. The potassium source may be potassium hydroxide. In embodiments when the Group 1 metal (M) is a mixture of sodium and potassium, the molar ratio of sodium ($m_1$) divided by the molar ratio of potassium ($m_2$) in the reaction mixture is less than or equal to 2.0; or less than or equal to 1.0; preferably, in the range from 0.1 to 2.0; and conveniently, in the range from 0.1 to 0.5.

Optionally, the reaction mixture may also include seeds of a molecular sieve material, such as SSZ-105 crystals from a previous synthesis, in an amount of from 0.1 to 10 wt. % or from 0.5 to 5 wt. % of the reaction mixture.

For each embodiment described herein, the molecular sieve reaction mixture can be supplied by more than one source. Also, two or more reaction components can be provided by one source.

The reaction mixture can be prepared either batch wise or continuously. Crystal size, morphology and crystallization time of the molecular sieve described herein can vary with the nature of the reaction mixture and the crystallization conditions.

Crystallization and Post-Synthesis Treatment

Crystallization of the molecular sieve disclosed herein can be carried out under either static, tumbled or stirred conditions in a suitable reactor vessel, such as for example polypropylene jars or Teflon-lined or stainless steel autoclaves, at a temperature of from 125° C. to 200° C. (e.g., from 140° C. to 180° C.) for a time sufficient for crystallization to occur at the temperature used, e.g., from 1 day to 28 days.

Once the molecular sieve crystals have formed, the solid product is separated from the reaction mixture by standard mechanical separation techniques such as centrifugation or filtration. The crystals are water-washed and then dried to obtain the as-synthesized molecular sieve crystals. The drying step is typically performed at a temperature of less than 200° C.

As a result of the crystallization process, the recovered crystalline molecular sieve product contains within its pore structure at least a portion of the structure directing agent used in the synthesis.

The structure directing agent is typically at least partially removed from the molecular sieve by calcination before use. Calcination consists essentially of heating the molecular sieve comprising the structure directing agent at a temperature of from 200° C. to 800° C. in the presence of an oxygen-containing gas, optionally in the presence of steam. The structure directing agent can also be removed by photolysis techniques as described in U.S. Pat. No. 6,960,327.

To the extent desired and depending on the composition of the molecular sieve, any cations in the as-synthesized or calcined molecular sieve can be replaced in accordance with techniques well known in the art by ion exchange with other cations. Preferred replacing cations include metal ions, hydrogen ions, hydrogen precursor, e.g., ammonium ions and mixtures thereof. Particularly preferred cations are those which tailor the catalytic activity for certain organic conversion reactions. These include hydrogen, rare earth metals and metals of Groups 2 to 15 of the Periodic Table of the Elements. As used herein, the term "as-synthesized" refers to the molecular sieve in its form after crystallization, prior to removal of the SDA cation.

The molecular sieve disclosed herein can be formulated with into a catalyst composition by combination with other materials, such as binders and/or matrix materials, which provide additional hardness or catalytic activity to the finished catalyst. When blended with such components, the relative proportions of the SSZ-105 molecular sieve and matrix may vary widely with the SSZ-105 content ranging from 1 to 99 wt. % (e.g., from 10 to 90 wt. % or from 20 to 80 wt. %) of the total catalyst.

Characterization of the Molecular Sieve

Molecular sieve SSZ-105 is an intergrowth of the ERI and LEV crystal structures. Physical mixtures of the two phases ERI and LEV prepared by mixing samples of two pure materials are not defined as molecular sieve SSZ-105.

In its as-synthesized and anhydrous form, molecular sieve SSZ-105 has a chemical composition, in terms of mole ratios, as described in Table 2:

TABLE 2

|  | Broad | Exemplary |
|---|---|---|
| $SiO_2/Al_2O_3$ | 10 to 50 | 15 to 40 |
| $Q/SiO_2$ | 0.02 to 0.20 | 0.05 to 0.20 |
| $M/SiO_2$ | 0.01 to 0.20 | 0.02 to 0.15 | wherein compositional variables Q and M are as described herein above.

It should be noted that the as-synthesized form of the molecular sieve disclosed herein may have molar ratios different from the molar ratios of reactants of the reaction mixture used to prepare the as-synthesized form. This result may occur due to incomplete incorporation of 100% of the reactants of the reaction mixture into the crystals formed (from the reaction mixture).

In its calcined form, molecular sieve SSZ-105 has chemical composition comprising the following molar relationship:

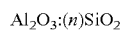

$Al_2O_3:(n)SiO_2$ wherein n has a value of at least 10 (e.g., from 10 to 50, from 10 to 45, from 10 to 40, from 10 to 35, from 10 to 30, from 10 to 25, from 12 to 50, from 12 to 45, from 12 to 40, from 12 to 35, from 12 to 30, from 12 to 25, from 15 to 50, from 15 to 45, from 15 to 40, from 15 to 35, from 15 to 30, or from 15 to 25).

In one embodiment, the intergrown crystalline molecular sieve disclosed herein can have from 1% to 99% (e.g., from 5% to 95%, from 10% to 90%, from 20% to 80%, from 30% to 70%, from 40% to 60%) of the ERI crystal structure. Similarly, the intergrown molecular sieve disclosed herein can have from 1% to 99% (e.g., from 5% to 95%, from 10% to 90%, from 20% to 80%, from 30% to 70%, or from 40% to 60%) of the LEV crystal structure. The relative proportions of each of the phases can be analyzed by X-ray diffraction and, in particular, by comparing the observed patterns with calculated patterns generated using algorithms to simulate the effects of stacking disorder. DIFFaX is a computer program based on a mathematical model for calculating intensities from faults (see M. M. J. Treacy et al., Proc. R. Soc. Lond. A 1991, 433, 499-520). DIFFaX is the simulation program selected by and available from the International Zeolite Association to simulate the powder XRD patterns for randomly intergrown phases (see "Collection of Simulated XRD Powder Patterns for Zeolites," Fifth Revised Edition, Elsevier, 2007).

The powder X-ray diffraction patterns presented herein were collected by standard techniques. The radiation was $CuK_\alpha$ radiation. The peak heights and the positions, as a function of 2θ where θ is the Bragg angle, were read from the relative intensities of the peaks (adjusting for background), and d, the interplanar spacing corresponding to the recorded lines, can be calculated.

Minor variations in the diffraction pattern can result from variations in the mole ratios of the framework species of the particular sample due to changes in lattice constants. In addition, sufficiently small crystals will affect the shape and intensity of peaks, leading to significant peak broadening. Minor variations in the diffraction pattern can also result from variations in the organic compound used in the preparation. Calcination can also cause minor shifts in the XRD pattern. Notwithstanding these minor perturbations, the basic crystal lattice structure remains unchanged.

Processes Using SSZ-105

Molecular sieve SSZ-105 can be used to dry gases and liquids; for selective molecular separation based on size and polar properties; as an ion-exchanger; as a chemical carrier; in gas chromatography; and as a catalyst in organic conversion reactions. Examples of suitable catalytic uses include catalytic conversion of oxygenates to one or more olefins, synthesis of monoalkylamines and dialkylamines, and catalytic reduction of nitrogen oxides.

Gas Separation

Molecular sieve SSZ-105 can be used to separate gases. For example, it can be used to separate carbon dioxide from natural gas. Typically, the molecular sieve is used as a component in a membrane that is used to separate the gases. Examples of such membranes are disclosed in U.S. Pat. No. 6,508,860.

Oxygenate Conversion

Molecular sieve SSZ-105 is useful in the catalytic conversion of oxygenates to one or more light olefins, i.e., $C_2$, $C_3$ and/or $C_4$ olefins. As used herein, the term "oxygenates" is defined to include aliphatic alcohols, ethers, carbonyl compounds (aldehydes, ketones, carboxylic acids, carbonates, and the like), and also compounds containing heteroatoms, such as, halides, mercaptans, sulfides, amines, and mixtures thereof. The aliphatic moiety will normally contain from 1 to 10 carbon atoms, such as from 1 to 4 carbon atoms.

Representative oxygenates include lower straight chain or branched aliphatic alcohols, their unsaturated counterparts, and their nitrogen, halogen and sulfur analogues. Examples of suitable oxygenate compounds include methanol, ethanol, n-propanol, isopropanol, $C_4$-$C_{10}$ alcohols, methyl ethyl ether, dimethyl ether, diethyl ether, diisopropyl ether, methyl mercaptan, methyl sulfide, methyl amine, ethyl mercaptan, diethyl sulfide, diethyl amine, ethyl chloride, formaldehyde, dimethyl carbonate, dimethyl ketone, acetic acid, n-alkyl amines, n-alkyl halides, n-alkyl sulfides having n-alkyl groups of comprising the range of from 3 to 10 carbon atoms, and mixtures thereof. Particularly suitable oxygenate compounds are methanol, dimethyl ether, or mixtures thereof, most preferably methanol. As used herein, the term "oxygenate" designates only the organic material used as the feed. The total charge of feed to the reaction zone may contain additional compounds, such as diluents.

In the present oxygenate conversion process, a feedstock comprising an organic oxygenate, optionally with one or more diluents, is contacted in the vapor phase in a reaction zone with a catalyst comprising the molecular sieve disclosed herein at effective process conditions so as to produce the desired olefins. Alternatively, the process may be carried out in a liquid or a mixed vapor/liquid phase. When the process is carried out in the liquid phase or a mixed vapor/liquid phase, different conversion rates and selectivities of feedstock-to-product may result depending upon the catalyst and the reaction conditions.

When present, the diluent(s) is generally non-reactive to the feedstock or molecular sieve catalyst composition and is typically used to reduce the concentration of the oxygenate in the feedstock. Non-limiting examples of suitable diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred. Diluent(s) may comprise from 1 to 99 mole % of the total feed mixture.

The temperature employed in the oxygenate conversion process may vary over a wide range, such as from 200° C. to 1000° C. (e.g., from 250° C. to 800° C., from 250° C. to 750° C., from 300° C. to 650° C., from 350° C. to 600° C., or from 400° C. to 600° C.).

Light olefin products will form, although not necessarily in optimum amounts, at a wide range of pressures, including autogenous pressures and pressures in the range of from 0.1 to 10 MPa (e.g., from 7 kPa to 5 MPa, or from 50 kPa to 1 MPa). The foregoing pressures are exclusive of diluent, if any is present, and refer to the partial pressure of the feedstock as it relates to oxygenate compounds and/or mixtures thereof. Lower and upper extremes of pressure may adversely affect selectivity, conversion, coking rate, and/or reaction rate; however, light olefins such as ethylene still may form.

The process should be continued for a period of time sufficient to produce the desired olefin products. The reaction time may vary from tenths of seconds to a number of hours. The reaction time is largely determined by the reaction temperature, the pressure, the catalyst selected, the weight hourly space velocity, the phase (liquid or vapor) and the selected process design characteristics.

A wide range of weight hourly space velocities (WHSV) for the feedstock will function in the present process. WHSV is defined as weight of feed (excluding diluent) per hour per weight of a total reaction volume of molecular sieve catalyst (excluding inerts and/or fillers). The WHSV generally should be in the range of from 0.01 $h^{-1}$ to 500 $h^{-1}$ (e.g., from 0.5 to 300 $h^{-1}$, or from 1 to 200 $h^{-1}$).

The molecular sieve catalyst can be incorporated into solid particles in which the catalyst is present in an amount effective to promote the desired conversion of oxygenates to light olefins. In one aspect, the solid particles comprise a catalytically effective amount of the catalyst and at least one matrix material selected from the group consisting of binder materials, filler materials and mixtures thereof to provide a desired property or properties, e.g., desired catalyst dilution, mechanical strength and the like to the solid particles. Such matrix materials are often, to some extent, porous in nature and can or cannot be effective to promote the desired reaction. Filler and binder materials include, for example, synthetic and naturally occurring substances such as metal oxides, clays, silicas, aluminas, silica-aluminas, silica-magnesias, silica-zirconias, silica-thorias and the like. If matrix materials are included in the catalyst composition, the molecular sieve desirably comprises from 1 to 99 wt. % (e.g., from 10 to 90 wt. %, or 20 to 80 wt. %) of the total composition.

Synthesis of Amines

Molecular sieve SSZ-105 can be used in a catalyst to prepare methylamine or dimethylamine. Dimethylamine is generally prepared in industrial quantities by continuous reaction of methanol (and/or dimethyl ether) and ammonia in the presence of a silica-alumina catalyst. The reactants are typically combined in the vapor phase, at temperatures of from 300° C. to 500° C., and at elevated pressures. Such a process is disclosed in U.S. Pat. No. 4,737,592.

The catalyst is used in its acid form. Acid forms of molecular sieves can be prepared by a variety of techniques. Desirably, the molecular sieve used to prepare dimethylamine will be in the hydrogen form, or have an alkali or alkaline earth metal, such as Na, K, Rb, or Cs, ion-exchanged into it.

The process disclosed herein involves reacting methanol, dimethyl ether, or a mixture thereof and ammonia in amounts sufficient to provide a carbon/nitrogen (C/N) ratio of from 0.2 to 1.5 (e.g., from 0.5 to 1.2). The reaction is conducted at a temperature of from 250° C. to 450° C. (e.g., from 300° C. to 400° C.). Reaction pressures can vary from 7 to 7000 kPa (e.g., from 70 to 3000 kPa). A methanol and/or dimethyl ether space time of from 0.01 to 80 $h^{-1}$ (e.g., from 0.10 to 1.5 $h^{-1}$) is typically used. This space time is calculated as the mass of catalyst divided by the mass flow rate of methanol/dimethyl ether introduced into the reactor.

Reduction of Oxides of Nitrogen

Molecular sieve SSZ-105 can be used for the catalytic reduction of the oxides of nitrogen in a gas stream. The catalyst comprises one or more metals supported on the molecular sieve support. Any suitable metal may be selected. Metals particularly effective for use during selective catalytic reduction include metals selected from the group consisting of Cr, Mn, Re, Mo, Fe, Ru, Co, Rh, Ir, Ni, Pd, Pt, Cu, Ag, Zn, Ga, In, Sn, and mixtures thereof. In one embodiment, the one or more metals is selected from the group consisting of Cr, Mn, Fe, Co, Rh, Ni, Pd, Pt, Cu, and mixtures thereof. Preferably, the metal is selected from Mn, Fe, Co, Pt, and Cu. More preferably, the one or more metals may be selected from the group consisting of Fe, Cu, and mixtures thereof. In an exemplary embodiment, the metal is Cu.

Any suitable and effective amount of at least one metal may be used in the catalyst. The total amount of the metal(s) that may be included in the molecular sieve may be from 0.01 to 20 wt. % (e.g., from 0.1 to 10 wt. %, from 0.5 to 5 wt. %, from 1 to 3 wt. %, or from 1.5 to 2.5 wt. %), based on the total weight of the catalyst.

The molecular sieve acts as a support for the metal, e.g., the metal may be inside the pore(s) and/or may be on the external surface of the molecular sieve. In an exemplary embodiment, a significant amount of the metal(s) resides inside the pores.

The metal(s) may also be included in the molecular sieve and/or supported by the molecular sieve using any feasible method. For example, the metal can be added after the molecular sieve has been synthesized, e.g., by incipient wetness or exchange process; or can be added during molecular sieve synthesis.

The molecular sieve catalysts may be used in any suitable form. For example, the molecular sieve catalyst may be used in powder form, as extrudates, as pellets, or in any other suitable form.

The molecular sieve catalysts for use herein may be coated on a suitable substrate monolith or can be formed as extruded-type catalysts, but are preferably used in a catalyst coating. In one embodiment, the molecular sieve catalyst is coated on a flow-through monolith substrate (i.e., a honeycomb monolithic catalyst support structure with many small, parallel channels running axially through the entire part) or filter monolith substrate, such as a wall-flow filter, etc. The molecular sieve catalyst for use herein may be coated, e.g., as a washcoat component, on a suitable monolith substrate, such as a metal or ceramic flow through monolith substrate or a filtering substrate, such as a wall-flow filter or sintered metal or partial filter (such as those disclosed in WO 01/80978 or EP 1057519). Alternatively, the molecular sieves for use herein may be synthesized directly onto the substrate and/or may be formed into an extruded-type flow through catalyst.

Washcoat compositions containing the molecular sieves for use herein for coating onto the monolith substrate for manufacturing extruded type substrate monoliths may comprise a binder, such as alumina, silica, (non-molecular sieve) silica-alumina, naturally occurring clays, such as $TiO_2$, $ZrO_2$, $SnO_2$, $CeO_2$, or mixtures thereof.

According to one embodiment, a method of using the catalyst comprises exposing a catalyst to at least one reactant in a chemical process. In other words, a method for reducing $NO_x$ in a gas comprises exposing the gas having at least one reactant, such as $NO_x$, to a catalyst. As used herein, a chemical process for reducing $NO_x$ in a gas can include any suitable chemical process using a catalyst comprising a molecular sieve or zeolite. Typical chemical processes include, but are not limited to, exhaust gas treatment such as selective catalytic reduction using nitrogenous reductants, lean $NO_x$ catalyst, catalyzed soot filter, or a combination of any one of these with a $NO_x$ adsorber catalyst or a three-way catalyst (TWC), e.g., NAC+(downstream)SCR or TWC+(downstream)SCR.

A method of treating $NO_x$ in an exhaust gas of a lean burn internal combustion engine is to store the $NO_x$ from a lean gas in a basic material and then to release the $NO_x$ from the basic material and reduce it periodically using a rich gas. The combination of a basic material (such as an alkali metal, alkaline earth metal, or a rare earth metal), and a precious metal (such as platinum), and possibly also a reduction catalyst component (such as rhodium) is typically referred to as a $NO_x$ adsorber catalyst (NAC), a lean $NO_x$ trap (LNT), or a $NO_x$ storage/reduction catalyst (NSRC). As used herein, $NO_x$ storage/reduction catalyst, $NO_x$ trap, and $NO_x$ adsorber catalyst (or their acronyms) may be used interchangeably.

Under certain conditions, during the periodically rich regeneration events, $NH_3$ may be generated over a $NO_x$ adsorber catalyst. The addition of a SCR catalyst downstream of the $NO_x$ adsorber catalyst may improve the overall system $NO_x$ reduction efficiency. In the combined system, the SCR catalyst is capable of storing the released $NH_3$ from the NAC catalyst during rich regeneration events and utilizes the stored $NH_3$ to selectively reduce some or all of the $NO_x$ that slips through the NAC catalyst during the normal lean operation conditions. As used herein, such combined systems may be shown as a combination of their respective acronyms, e.g., NAC+SCR or LNT+SCR.

The catalysts may be effective in reducing or lean conditions, e.g., as encountered in engine emissions. For example, the lean portion of the cycle may consist of exposure to about 200 ppm NO, 10% $O_2$, 5% $H_2O$, 5% $CO_2$ in $N_2$, and the rich portion of the cycle may consist of exposure to about 200 ppm NO, 5000 ppm $C_3H_6$, 1.3% $H_2$, 4% CO, 1% $O_2$, 5% $H_2O$, 5% $CO_2$ in $N_2$. A reducing atmosphere is an atmosphere having a lambda value of less than 1, i.e., the redox composition is net reducing. A lean atmosphere is one having a lambda value of greater than 1, i.e., the redox composition is net oxidizing. The catalysts described herein may be particularly effective when exposed to a reducing atmosphere, more particularly a high temperature reducing atmosphere, such as when encountered during the rich phase of a lean/rich excursion cycle.

A method for reducing $NO_x$ in a gas comprises exposing the gas having at least one reactant to a catalyst. The reactant may include any reactants typically encountered in the chemical processes above. Reactants may include a selective catalytic reductant, such as ammonia. Selective catalytic reduction may include (1) using ammonia or a nitrogenous reductant or (2) a hydrocarbon reductant (the latter also known as lean $NO_x$ catalysis). Other reactants may include nitrogen oxides and oxygen. In an exemplary embodiment, the catalysts described herein are used during selective catalytic reduction of $NO_x$ with ammonia.

The at least one reactant, e.g., nitrogen oxides, is reduced with the reducing agent at a temperature of at least 100° C. (e.g., from 150° C. to 750° C., or from 175° C. to 550° C.).

For a reactant including nitrogen oxides, the reduction of nitrogen oxides may be carried out in the presence of oxygen or in the absence of oxygen. The source of nitrogenous reductant can be ammonia, hydrazine, ammonium carbonate, ammonium carbamate, ammonium hydrogen carbonate, ammonium formate or any suitable ammonia precursor, such as urea.

The method may be performed on a gas derived from a combustion process, such as from an internal combustion engine (whether mobile or stationary), a gas turbine and coal or oil fired power plants. The method may also be used to treat gas from industrial processes such as refining, from refinery heaters and boilers, furnaces, the chemical processing industry, coke ovens, municipal waste plants and incinerators, coffee roasting plants, etc.

In a particular embodiment, the method is used for treating exhaust gas from a vehicular internal combustion engine with a lean/rich cycle, such as a diesel engine, a gasoline engine, or an engine powered by liquid petroleum gas or natural gas.

For a reactant including nitrogen oxides, the nitrogenous reductant may be metered into the flowing exhaust gas only when it is determined that the molecular sieve catalyst is capable of catalyzing $NO_x$ reduction at or above a desired efficiency, such as at above 100° C., above 150° C., or above 175° C. The determination by the control means can be assisted by one or more suitable sensor inputs indicative of a condition of the engine selected from the group consisting of: exhaust gas temperature, catalyst bed temperature, accelerator position, mass flow of exhaust gas in the system, manifold vacuum, ignition timing, engine speed, lambda value of the exhaust gas, the quantity of fuel injected in the engine, the position of the exhaust gas recirculation (EGR) valve and thereby the amount of EGR and boost pressure.

Metering may be controlled in response to the quantity of nitrogen oxides in the exhaust gas determined either directly (using a suitable $NO_x$ sensor) or indirectly, such as using pre-correlated look-up tables or maps—stored in the control means—correlating any one or more of the abovementioned inputs indicative of a condition of the engine with predicted $NO_x$ content of the exhaust gas.

The molecular sieve supported metal catalysts described herein may exhibit improved $NH_3$—SCR activity, good thermal stability, good hydrothermal stability, and tolerate repeated lean/rich high temperature aging.

Treatment of Engine Exhaust (Cold Start Emissions)

Molecular sieve SSZ-105 can also be used as a hydrocarbon trap, particularly for reducing the emissions associated with the combustion of hydrocarbon fuels.

Increasingly lower emissions standards for vehicles are forcing automobile and catalyst manufacturers to focus on reducing cold start hydrocarbon emissions since a large portion of hydrocarbon emissions occur during the cold start period. Consequently, control of emissions during the cold start operation of a vehicle containing an internal combustion engine is essential. Vehicles equipped with a conventional three-way catalytic converter typically contain precious metals supported on a washcoat layer, which in turn is deposited on a monolithic carrier. Fresh catalysts start to operate at about 170° C., while aged catalysts work only at about 200° C. to 225° C. These catalysts usually require at least 1-2 minutes before reaching such temperatures, and during this "cold start" period, 70% to 80% of the tailpipe hydrocarbon emissions occur. Such cold start emissions often result in failure in the cycle of the U.S. Federal Test Procedure (FTP), a standardized laboratory method for new vehicles testing that is based on two simulated environments; namely, city and highway, in which prototypes of new vehicle models are driven by a trained driver in a laboratory on a dynamometer. At lower temperatures where the catalyst in a catalytic converter is not able to effectively convert incompletely burned hydrocarbons to final combustion products, a hydrocarbon adsorber system should trap hydrocarbons exhausted from the engine before they reach the catalytic converter by adsorbing the incompletely burned hydrocarbons. In the ideal case, desorption should occur at temperatures exceeding catalyst light-off.

The critical factors for any emission hydrocarbon trap are the adsorption capacity of the adsorbent, the desorption temperature at which adsorbed hydrocarbons are desorbed and passed to the catalytic converter (must be higher than the catalyst operating temperature), and the hydrothermal stability of the adsorbent. Molecular sieves such as zeolites have generally been found to be useful adsorbents for this application in part due to their hydrothermal stability under these conditions compared to other materials.

A method of treating exhaust gas is disclosed that comprises a hydrocarbon combustion product is provided, the method comprising contacting the exhaust gas with molecular sieve SSZ-105 for a time period effective to facilitate adsorption of the hydrocarbon combustion product by the molecular sieve; passing a purge gas through the molecular sieve to remove adsorbed hydrocarbon combustion product therefrom; and contacting the purge gas containing the removed hydrocarbon combustion product with a hydrocarbon conversion catalyst. The phrase "method of treating exhaust gas" generally refers to a method of reducing the emission of exhaust gas pollutants, particularly those associated with the incomplete combustion of hydrocarbon fuels. While not exclusively limited thereto, the treatment method is primarily directed to reducing the emission of incompletely combusted exhaust gas components, such as occur during the cold start operation of an internal combustion engine.

Exhaust gases produced from the combustion of a hydrocarbon fuels in an internal combustion engine contain a plurality of combustion components, typically including linear and branched chain non-aromatic hydrocarbons, cycloaliphatic hydrocarbons, aromatic hydrocarbons, polycyclic hydrocarbons and mixtures thereof, as well as non-hydrocarbon components such as carbon dioxide, water, nitrogen oxides and sulfur dioxide. Included within such emissions compounds are aromatic hydrocarbons such as toluene, xylene, benzene and mixtures thereof; linear and branched hydrocarbons such as methane, ethane, ethylene, propane, propylene, butane, pentane, hexane, heptane, octane; cycloaliphatic hydrocarbons such as cyclohexane; and additional fuel additives such as alcohols and methyl tertiary butyl ether (MTBE). The method disclosed herein may be advantageously utilized to reduce such hydrocarbon emissions, particularly during cold start operation of an internal combustion engine, without being necessarily limited to a particular hydrocarbon fuel. Typical hydrocarbon fuels benefiting from the present invention include gasolines, diesel fuels, aviation fuels, and the like.

The method may be applied as a batch process in which the adsorbent is contacted with the exhaust gas batchwise or as a continuous or semi-continuous process in which the exhaust gas continuously or semi-continuously flows through the molecular sieve. For example, the method may be applied as a continuous process for purifying the exhaust gas from an internal combustion engine in which a hydrocarbon fuel is combusted. In such a continuous process, the exhaust gas may be first passed from the source, such as from an internal combustion engine, to an adsorbent molecular sieve (i.e., SSZ-105), so that components in the exhaust gas, particularly hydrocarbons, are adsorbed by the molecular sieve. Depending on the application, the adsorbed components are typically subsequently desorbed from the molecular sieve and brought into contact with a catalyst. In the case of an exhaust gas purification system, SSZ-105 may be utilized to adsorb partially combusted hydrocarbon components from the exhaust gas of an internal combustion engine by contacting the molecular sieve with the exhaust gas upstream of a catalytic converter. As the molecular sieve and the catalyst subsequently heat up due to continued throughflow of the exhaust gas, the components adsorbed onto the molecular sieve are desorbed into the exhaust gas stream and passed on to the converter. The desorbed hydrocarbon components are then converted by the catalyst due to the improved hydrocarbon conversion efficiency of the catalyst at higher operating temperatures.

The method disclosed herein may also be carried out sequentially and continuously with a flowing exhaust gas, that is, wherein the exhaust gas continuously flows through the molecular sieve and then through a downstream catalytic converter. In this regard, the exhaust gas may also essentially function as the purge gas for removing exhaust components desorbed from the molecular sieve. A separate purge gas stream, or a separate purge gas stream in conjunction with the exhaust gas stream, may also be used to remove the desorbed exhaust gas components, including, without limitation, air such as secondary air that is added to the exhaust gas stream, an inert gas, or a mixture thereof.

The use of SSZ-105 in batch and semi-continuous systems is also within the scope of this disclosure. For example, in a batch process SSZ-105 may be contacted with a portion of the exhaust gas such that the exhaust gas components, particularly incompletely combusted hydrocarbon components produced during cold start operation of an internal combustion engine, are adsorbed onto the molecular sieve. Thereafter, when the operating temperature of a catalyst such as in a catalytic converter has been reached, the adsorbed components may be purged using a purge gas and passed to the catalyst for conversion to exhaust gas emission products. Similarly, in a semi-continuous process, the exhaust gas may be initially passed through the molecular sieve and subsequently through a downstream catalyst. After a period of time (e.g., when the catalyst light-off temperature is reached), the exhaust gas may be re-directed to pass only through the catalyst, such that the molecular sieve is bypassed. A purge gas such as air may then be passed through the molecular sieve to desorb the exhaust gas components adsorbed onto the molecular sieve.

In one embodiment, the SSZ-105 molecular sieve may also contain a metal cation selected from rare earth, Group 2 metals, Groups 6-12 metals, and mixtures thereof (e.g., the metal cation may be selected from Mg, Ca, Mn, Fe, Co, Ni, Pd, Pt, Cu, Ag, Au, Zn, Cd, and mixtures thereof). In an alternate embodiment, the molecular sieve contains a metal selected from Cu, Ag, Au and mixtures thereof.

Although the molecular sieve may be utilized to adsorb exhaust gas components by itself, it may also be utilized in an adsorbent material that comprises the molecular sieve along with additional materials such as binders and clays. The adsorbent material may also comprise one or more catalysts in conjunction with the molecular sieve. Such catalysts are generally known in the art and are not specifically limited for use herein in conjunction with the adsorbent material. Other adsorbent materials may also be included along with molecular sieve SSZ-105 if desired, including without limitation molecular sieves having a framework type such as, e.g., AEI, AFX, *BEA, CHA, CON, IFR, MTT, MWW, MTW, SEW, SFE, SFF, SFG, SFH, SFN, SFS, *SFV, SSY, STF, STT, —SVR, and mixtures thereof, and the like.

EXAMPLES

The following illustrative examples are intended to be non-limiting.

Example 1

0.80 g of 45% KOH solution, 0.13 g of 50% NaOH solution, 9.56 g of deionized water and 2.00 g of CBV760 Y-zeolite powder (Zeolyst International, $SiO_2/Al_2O_3$ mole ratio=60) were mixed together in a Teflon liner. Then, 8.45 g of 20% N,N-dimethylpiperidinium hydroxide solution was added to the mixture. The resulting gel was stirred until it became homogeneous. The liner was then capped and placed within a Parr steel autoclave reactor. The autoclave was then placed in an oven and the heated at 150° C. for 4 days. The solid products were recovered by centrifugation, washed with deionized water and dried at 95° C.

The resulting product had a $SiO_2/Al_2O_3$ mole ratio of 15.8, as determined by ICP elemental analysis.

Figure 2:
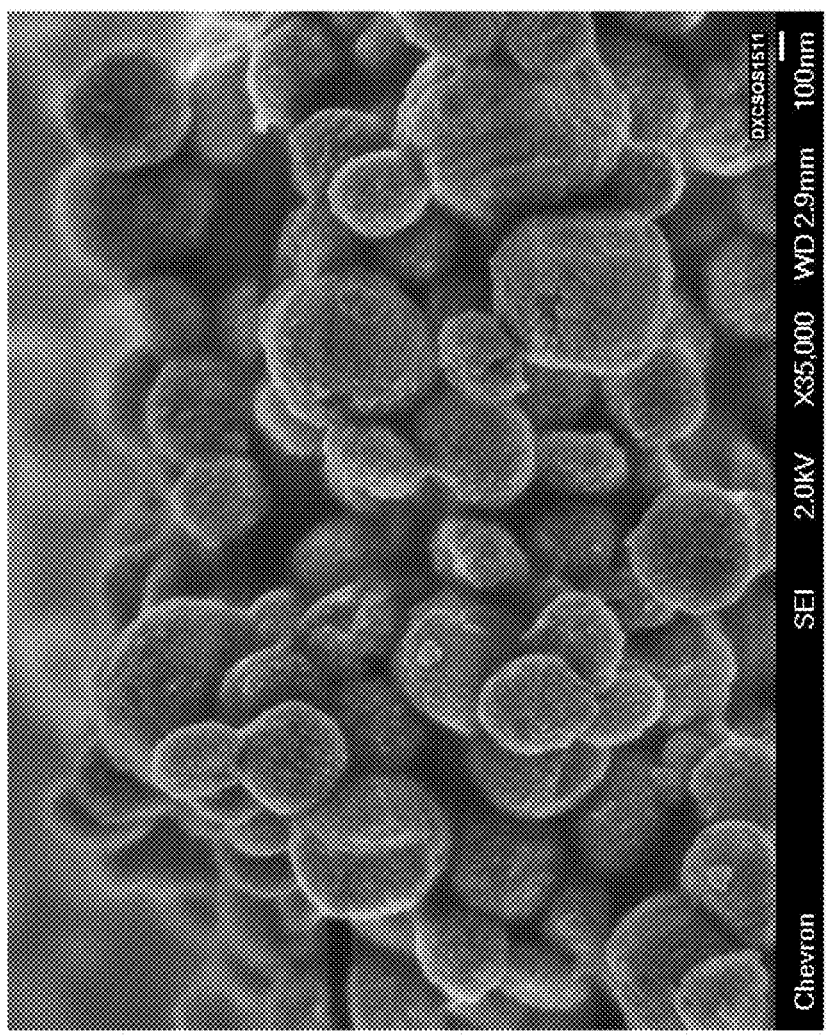
FIG. 2 is a Scanning Electron Micrograph (SEM) image of the as-synthesized molecular sieve prepared in Example 1.

The resulting product was analyzed by powder XRD and SEM. The powder XRD pattern is shown in FIG. 1. The SEM image is shown in FIG. 2 and indicates a uniform field of crystals. The list of the characteristic XRD peaks for this as-synthesized product is shown in Table 3 below.

TABLE 3

Characteristic Peaks for As-Synthesized SSZ-105 Prepared in Example 1

| 2-Theta[a] | d-Spacing, nm | Relative Intensity[b] |
|---|---|---|
| 7.86 | 1.124 | S |
| 11.00 | 0.804 | S |
| 11.76 | 0.752 | W |
| 13.54 | 0.654 | M |
| 15.64 | 0.566 | W |
| 17.49 | 0.507 | S |
| 17.94 | 0.494 | S |
| 20.72 | 0.428 | M |
| 22.10 | 0.402 | VS |
| 23.54 | 0.378 | S |

[a]±0.35
[b]The powder XRD patterns provided are based on a relative intensity scale in which the strongest line in the powder X-ray diffraction pattern is assigned a value of 100: W = weak (>0 to ≤20); M = medium (>20 to ≤40); S = strong (>40 to ≤60); VS = very strong (>60 to ≤100).

Figure 3:
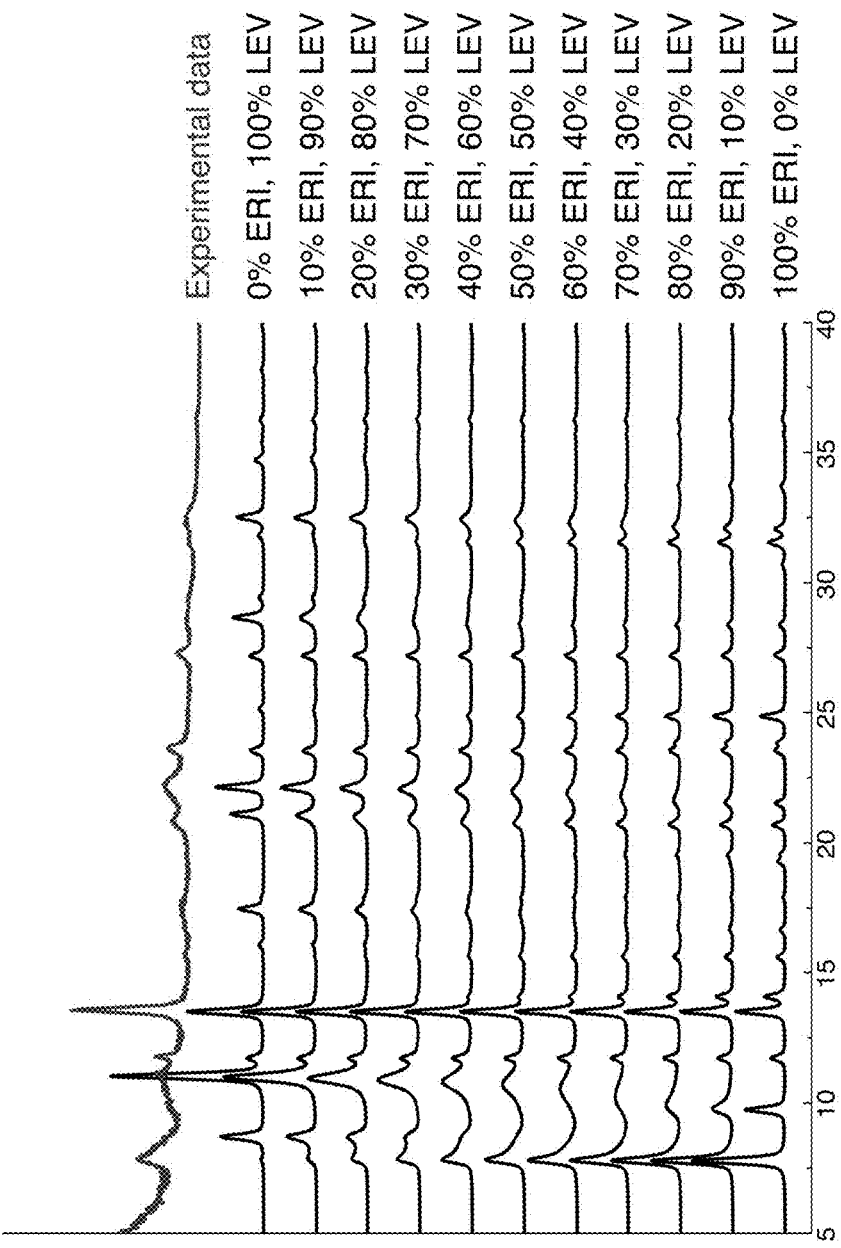
FIG. 3 is a plot of several DIFFaX-generated simulated XRD patterns and a powder XRD pattern of the calcined form of the molecular sieve prepared in Example 1.

A comparison between the experimental powder XRD pattern collected from the calcined product and DIFFaX simulated powder XRD patterns with various ERI/LEV intergrowth ratios is shown in FIG. 3. DIFFaX calculation indicates that the product is an intergrowth material with approximately 50-60% of ERI stacking sequence and 40-50% LEV stacking sequence.

Example 2

3.21 g of 45% KOH solution, 0.52 g of 50% NaOH solution, 32.46 g of deionized water and 8.00 g of CBV780 Y-zeolite powder (Zeolyst International, $SiO_2/Al_2O_3$ mole ratio=80) were mixed together in a Teflon liner. Then, 41.05 g of 20% N,N-dimethylpiperidinium hydroxide solution was added to the mixture. The resulting gel was stirred until it became homogeneous. The liner was then capped and placed within a Parr steel autoclave reactor. The autoclave was then placed in an oven and the heated at 150° C. for 3 days. The solid products were recovered by centrifugation, washed with deionized water and dried at 95° C.

The resulting product had a $SiO_2/Al_2O_3$ mole ratio of 17.1, as determined by ICP elemental analysis.

Figure 4:
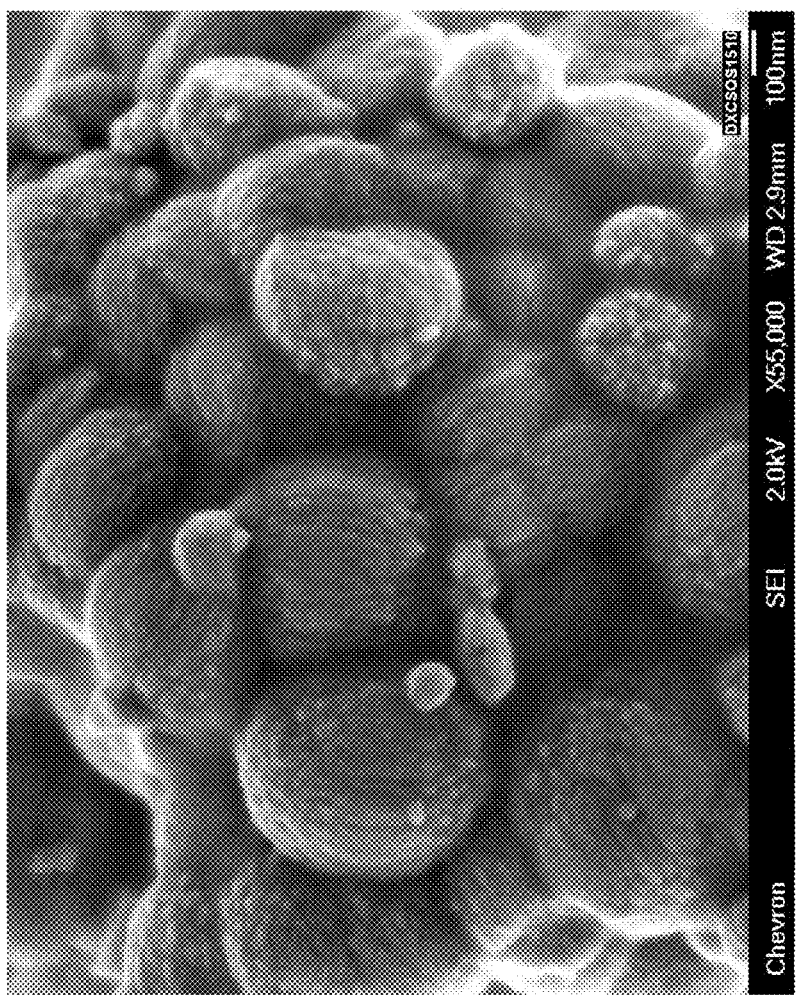
FIG. 4 is a SEM image of the as-synthesized molecular sieve prepared in Example 2.

The resulting product was identified by powder XRD and SEM as pure SSZ-105. The SEM image is shown in FIG. 4. The list of the characteristic XRD peaks for this as-synthesized product is shown in Table 4 below.

TABLE 4

Characteristic Peaks for As-Synthesized SSZ-105 Prepared in Example 2

| 2-Theta[a] | d-Spacing, nm | Relative Intensity[b] |
|---|---|---|
| 7.90 | 1.118 | S |
| 11.00 | 0.804 | S |
| 11.73 | 0.754 | W |
| 13.51 | 0.655 | W |
| 15.78 | 0.561 | W |
| 17.48 | 0.507 | S |
| 17.90 | 0.495 | M |
| 20.86 | 0.425 | M |

TABLE 4-continued

Characteristic Peaks for As-Synthesized SSZ-105 Prepared in Example 2

| 2-Theta[a] | d-Spacing, nm | Relative Intensity[b] |
|---|---|---|
| 22.28 | 0.399 | VS |
| 23.52 | 0.378 | M |

[a] ±0.35
[b] The powder XRD patterns provided are based on a relative intensity scale in which the strongest line in the powder X-ray diffraction pattern is assigned a value of 100: W = weak (>0 to ≤20); M = medium (>20 to ≤40); S = strong (>40 to ≤60); VS = very strong (>60 to ≤100).

Figure 5:
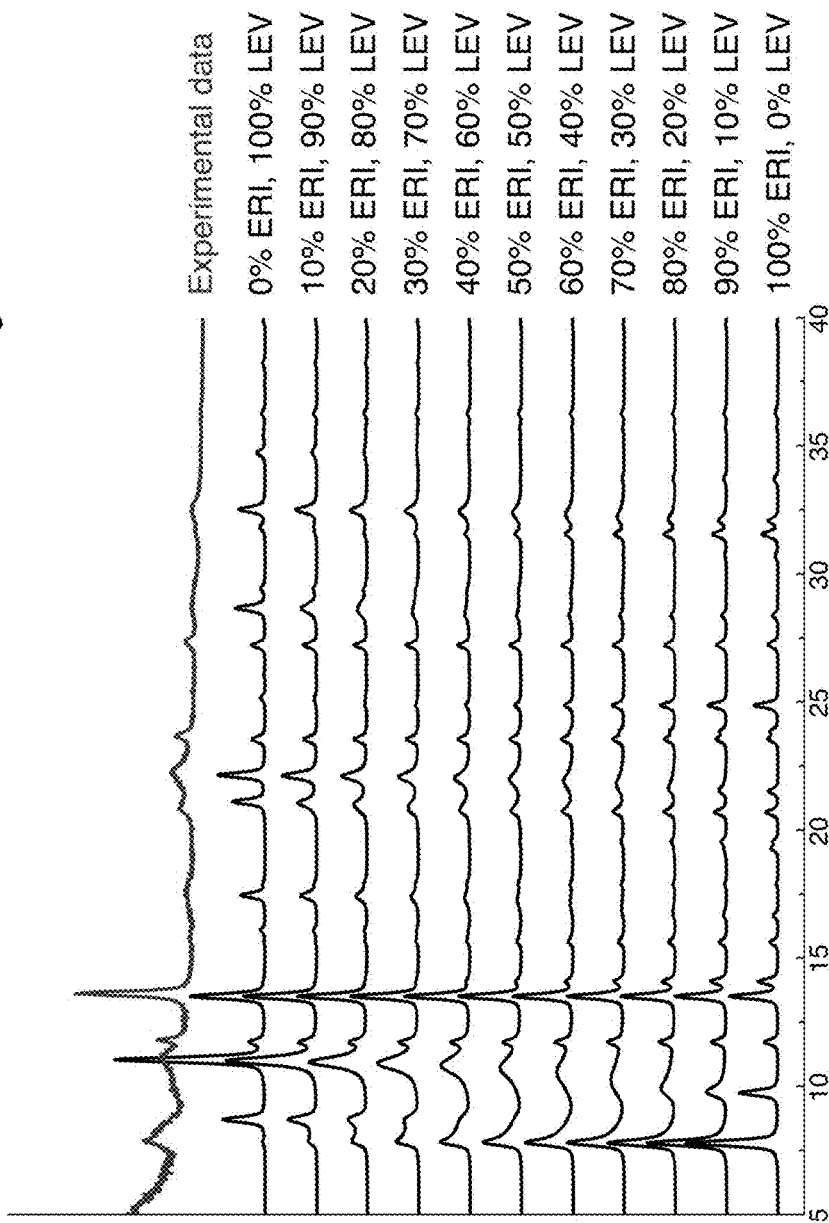
FIG. 5 is a plot of several DIFFaX-generated simulated XRD patterns and a powder XRD pattern of the calcined form of the molecular sieve prepared in Example 2.

A comparison between the experimental powder XRD pattern collected from the calcined product and DIFFaX simulated powder XRD patterns with various ERI/LEV intergrowth ratios is shown in FIG. 5. DIFFaX calculation indicates that the product is an intergrowth material with approximately 50-60% of ERI stacking sequence and 40-50% LEV stacking sequence.

Example 3

0.80 g of 45% KOH solution, 0.13 g of 50% NaOH solution, 9.56 g of deionized water and 2.00 g of CBV720 Y-zeolite powder (Zeolyst International, $SiO_2/Al_2O_3$ mole ratio=30) were mixed together in a Teflon liner. Then, 8.45 g of 20% N,N-dimethylpiperidinium hydroxide solution was added to the mixture. The resulting gel was stirred until it became homogeneous. The liner was then capped and placed within a Parr steel autoclave reactor. The autoclave was then placed in an oven and the heated at 150° C. for 4 days. The solid products were recovered by centrifugation, washed with deionized water and dried at 95° C.

The resulting product had a $SiO_2/Al_2O_3$ mole ratio of 12.7, as determined by ICP elemental analysis.

Figure 6:
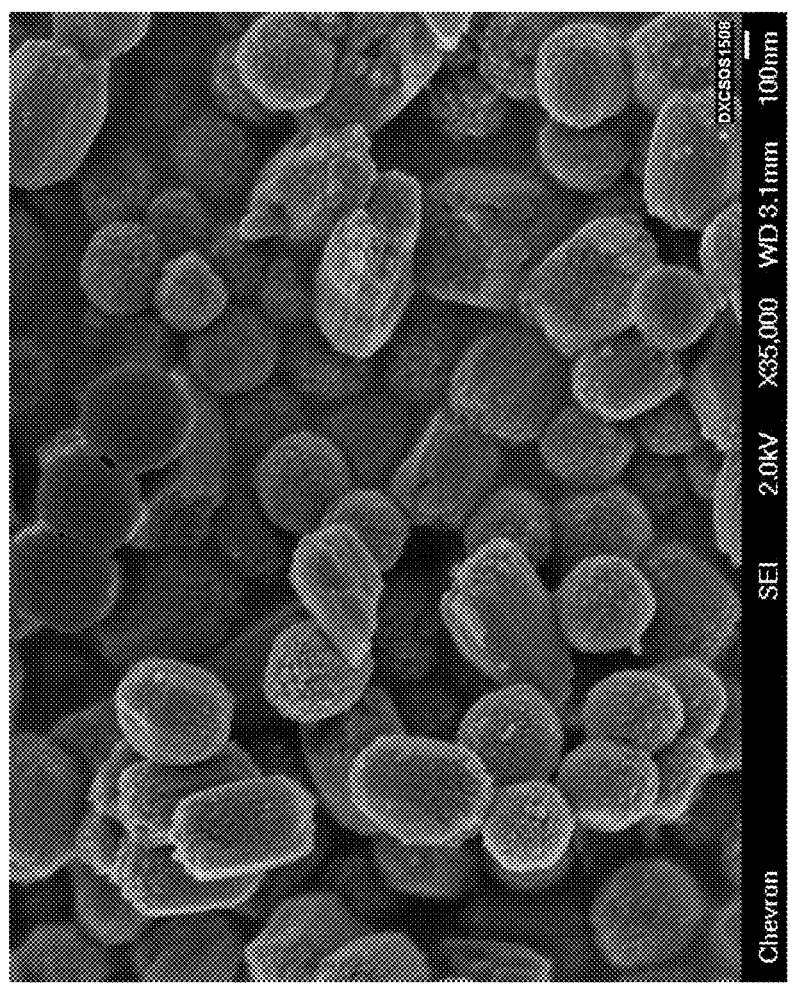
FIG. 6 is a SEM image of the as-synthesized molecular sieve prepared in Example 3.

The resulting product was identified by powder XRD and SEM as pure SSZ-105. The SEM image is shown in FIG. 6. The list of the characteristic XRD peaks for this as-synthesized product is shown in Table 5 below.

TABLE 5

Characteristic Peaks for As-Synthesized SSZ-105 Prepared in Example 3

| 2-Theta[a] | d-Spacing, nm | Relative Intensity[b] |
|---|---|---|
| 7.80 | 1.132 | VS |
| 9.80 | 0.902 | M |
| 11.76 | 0.752 | W |
| 13.47 | 0.657 | S |
| 15.56 | 0.569 | M |
| 16.68 | 0.531 | W |
| 17.90 | 0.495 | W |
| 19.36 | 0.458 | S |
| 20.65 | 0.430 | M |
| 21.45 | 0.414 | W |

[a] ±0.35
[b] The powder XRD patterns provided are based on a relative intensity scale in which the strongest line in the powder X-ray diffraction pattern is assigned a value of 100: W = weak (>0 to ≤20); M = medium (>20 to ≤40); S = strong (>40 to ≤60); VS = very strong (>60 to ≤100).

Figure 7:
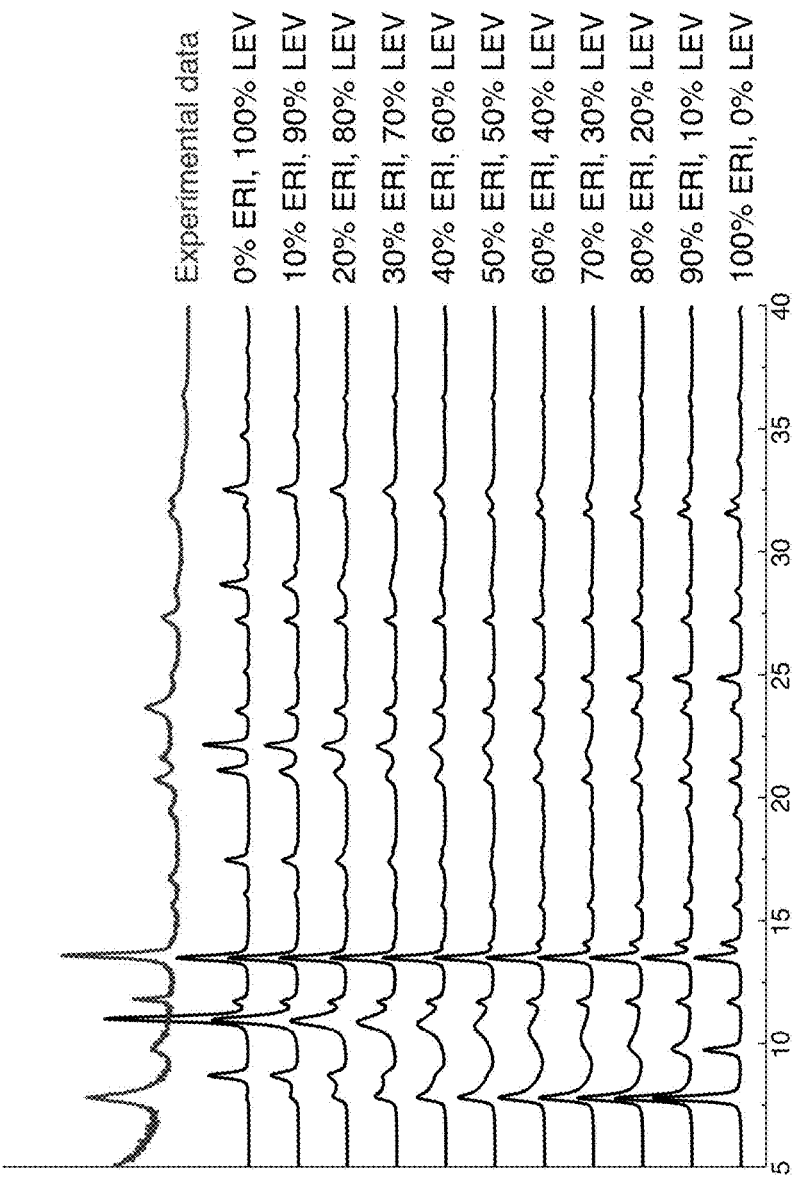
FIG. 7 is a plot of several DIFFaX-generated simulated XRD patterns and a powder XRD pattern of the calcined form of the molecular sieve prepared in Example 3.

A comparison between the experimental powder XRD pattern collected from the calcined product and DIFFaX simulated powder XRD patterns with various ERI/LEV intergrowth ratios is shown in FIG. 7. DIFFaX calculation indicates that the product is an intergrowth material with approximately 80-90% of ERI stacking sequence and 10-20% LEV stacking sequence.

Example 4

3.21 g of 45% KOH solution, 32.72 g of deionized water and 8.00 g of CBV760 Y-zeolite powder (Zeolyst International, $SiO_2/Al_2O_3$ mole ratio=60) were mixed together in a Teflon liner. Then, 41.05 g of 20% N,N-dimethylpiperidinium hydroxide solution was added to the mixture. The resulting gel was stirred until it became homogeneous. The liner was then capped and placed within a Parr steel autoclave reactor. The autoclave was then placed in an oven and the heated at 150° C. for 3 days. The solid products were recovered by centrifugation, washed with deionized water and dried at 95° C.

The resulting product had a $SiO_2/Al_2O_3$ mole ratio of 19.7, as determined by ICP elemental analysis.

Figure 8:
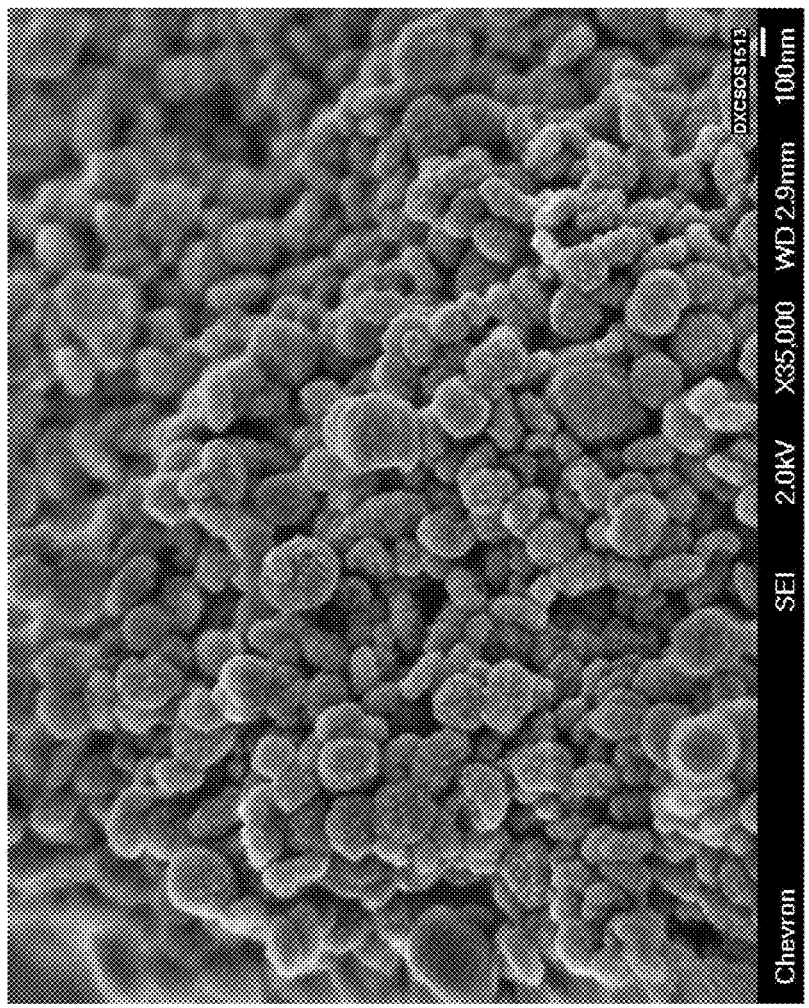
FIG. 8 is a SEM image of the as-synthesized molecular sieve prepared in Example 4.

The resulting product was analyzed by powder XRD and SEM. It was identified as pure SSZ-105 molecular sieve. The SEM image is shown in FIG. 8. The list of the characteristic XRD peaks for this as-synthesized product is shown in Table 6 below.

TABLE 6

Characteristic Peaks for As-Synthesized SSZ-105 Prepared in Example 4.

| 2-Theta[a] | d-Spacing, nm | Relative Intensity[b] |
|---|---|---|
| 7.84 | 1.126 | W |
| 8.62 | 1.025 | W |
| 10.92 | 0.809 | S |
| 11.73 | 0.754 | W |
| 13.55 | 0.653 | S |
| 15.69 | 0.564 | W |
| 17.56 | 0.505 | VS |
| 17.92 | 0.495 | S |
| 21.06 | 0.421 | M |
| 22.28 | 0.399 | VS |

[a] ±0.35
[b] The powder XRD patterns provided are based on a relative intensity scale in which the strongest line in the powder X-ray diffraction pattern is assigned a value of 100: W = weak (>0 to ≤20); M = medium (>20 to ≤40); S = strong (>40 to ≤60); VS = very strong (>60 to ≤100).

Figure 9:
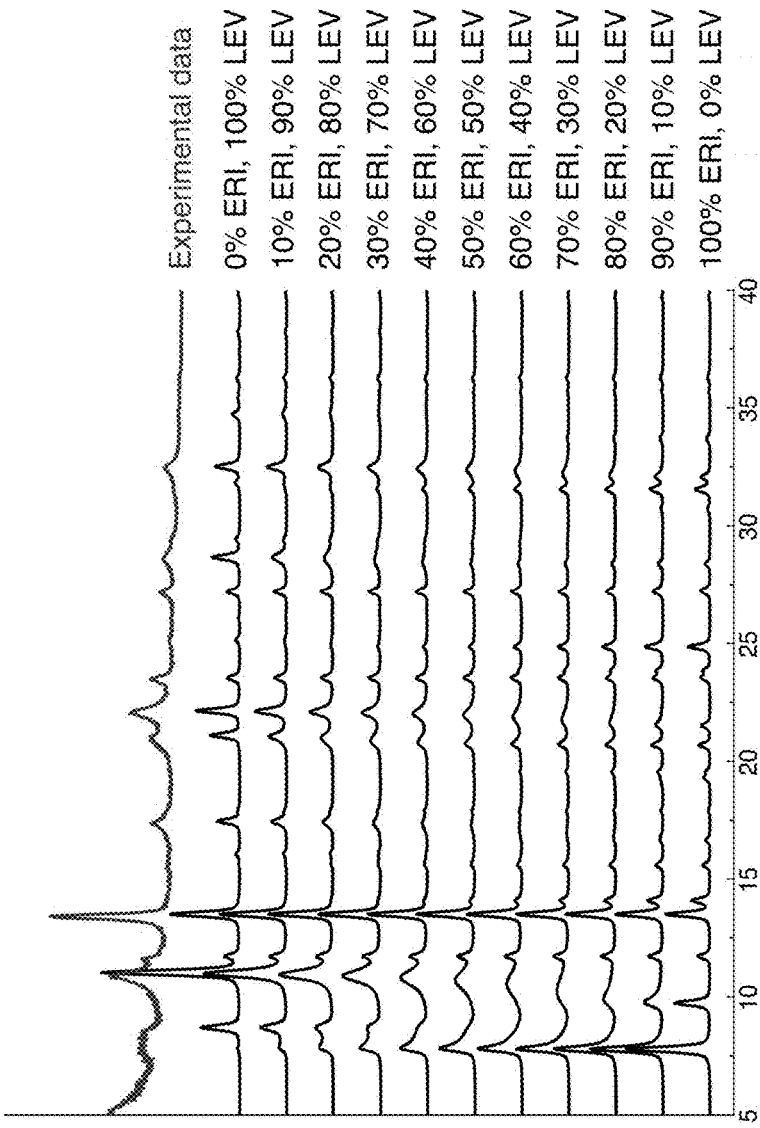
FIG. 9 is a plot of several DIFFaX-generated simulated XRD patterns and a powder XRD pattern of the calcined form of the molecular sieve prepared in Example 4.

A comparison between the experimental powder XRD pattern collected from the calcined product and DIFFaX simulated powder XRD patterns with various ERI/LEV intergrowth ratios is shown in FIG. 9. DIFFaX calculation indicates that the product is an intergrowth material with approximately 20-30% of ERI stacking sequence and 70-80% LEV stacking sequence.

Example 5

0.80 g of 45% KOH solution, 8.18 g of deionized water and 2.00 g of CBV780 Y-zeolite powder (Zeolyst International, $SiO_2/Al_2O_3$ mole ratio=80) were mixed together in a Teflon liner. Then, 10.26 g of 20% N,N-dimethylpiperidinium hydroxide solution was added to the mixture. The resulting gel was stirred until it became homogeneous. The liner was then capped and placed within a Parr steel autoclave reactor. The autoclave was then placed in an oven and the heated at 150° C. for 4 days. The solid products were recovered by centrifugation, washed with deionized water and dried at 95° C.

The resulting product had a $SiO_2/Al_2O_3$ mole ratio of 21.6, as determined by ICP elemental analysis.

Figure 10:
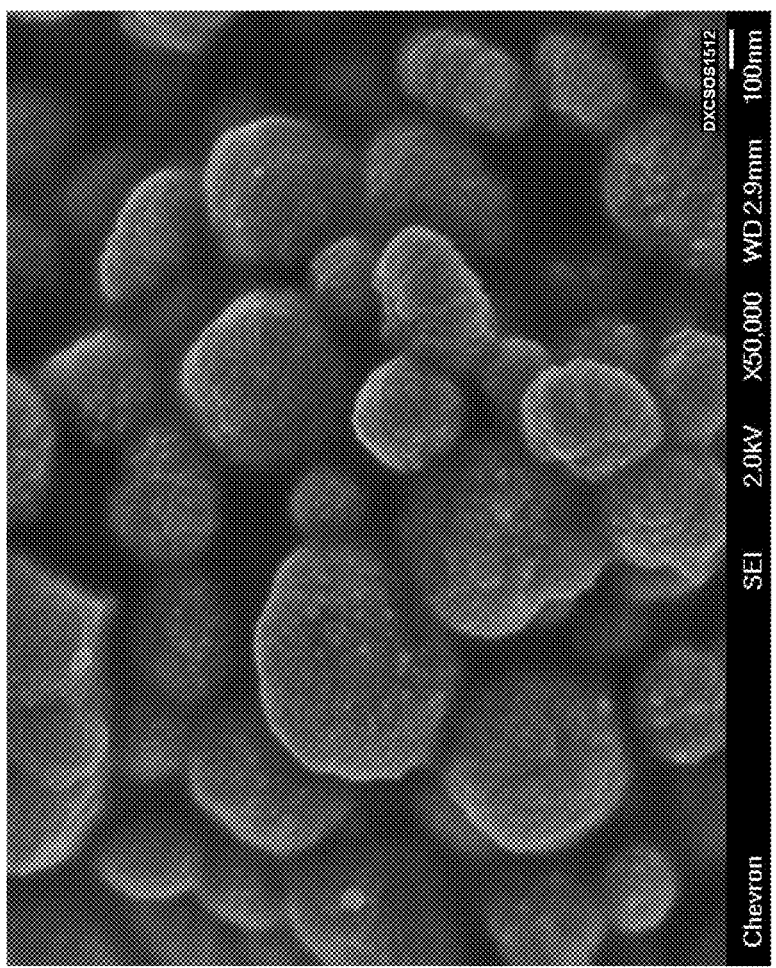
FIG. 10 is a SEM image of the as-synthesized molecular sieve prepared in Example 5.

The resulting product was analyzed by powder XRD and SEM and indicated that the product was pure SSZ-105 molecular sieve. The SEM image is shown in FIG. 10. The list of the characteristic XRD peaks for this as-synthesized product is shown in Table 7 below.

TABLE 7

Characteristic Peaks for As-Synthesized SSZ-105 Prepared in Example 5

| 2-Theta[a] | d-Spacing, nm | Relative Intensity[b] |
|---|---|---|
| 7.95 | 1.111 | W |
| 8.63 | 1.024 | W |
| 10.97 | 0.806 | M |
| 11.62 | 0.761 | W |
| 13.54 | 0.654 | M |
| 16.00 | 0.554 | W |
| 17.46 | 0.507 | VS |
| 17.88 | 0.496 | M |
| 21.06 | 0.421 | S |
| 22.22 | 0.400 | VS |

[a]±0.35
[b]The powder XRD patterns provided are based on a relative intensity scale in which the strongest line in the powder X-ray diffraction pattern is assigned a value of 100: W = weak (>0 to ≤20); M = medium (>20 to ≤40); S = strong (>40 to ≤60); VS = very strong (>60 to ≤100).

Figure 11:
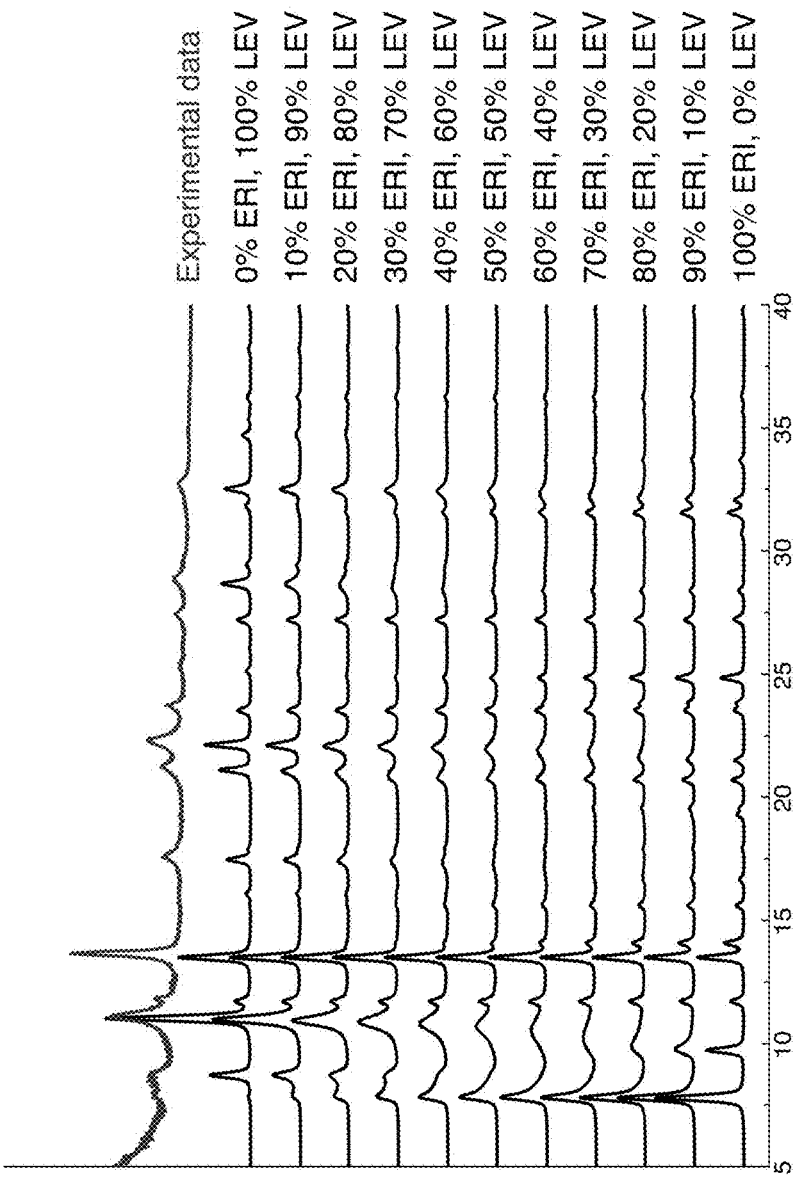
FIG. 11 is a plot of several DIFFaX-generated simulated XRD patterns and a powder XRD pattern of the calcined form of the molecular sieve prepared in Example 5.

A comparison between the experimental powder XRD pattern collected from the calcined product and DIFFaX simulated powder XRD patterns with various ERI/LEV intergrowth ratios is shown in FIG. 11. DIFFaX calculation indicates that the product is an intergrowth material with approximately 10-20% of ERI stacking sequence and 80-90% LEV stacking sequence.

Example 6

Calcination of SSZ-105

The as-synthesized molecular sieve products were calcined inside a muffle furnace under a flow of air heated to 540° C. at a rate of 1° C./minute and held at 540° C. for 5 hours, cooled and then analyzed by powder XRD.

FIG. 3, FIG. 5, FIG. 7, FIG. 9 and FIG. 11 show the XRD patterns of calcined SSZ-105 molecular sieve products 1, 2, 3, 4 and 5, respectively, and indicate that the material remains stable after calcination to remove the organic SDA.

Example 7

Micropore Volume Analysis

The calcined material from Example 6 was treated with 10 mL (per g of molecular sieve) of a 1N ammonium nitrate solution at 90° C. for 2 hours. The solution was cooled, decanted off and same process repeated.

The ammonium-exchanged molecular sieve product ($NH_4$-SSZ-105) was subjected to a micropore volume analysis using $N_2$ as adsorbate and via the BET method. The molecular sieve exhibited a micropore volume of 0.25 $cm^3/g$ and indicates that SSZ-105 has microporous character.

Example 8

Methanol Conversion

Ammonium-exchanged SSZ-105 was pelletized at 5 kpsi, crushed and meshed to 20-40. 0.20 g of catalyst (diluted 4:1 v/v with alundum) was centered in a stainless steel down-flow reactor in a split tube furnace. The catalyst was pre-heated in-situ under flowing nitrogen at 400° C. A feed of pure methanol was introduced into the reactor at a rate of 0.324 $cm^3/h$ for 1.3 $h^{-1}$ WHSV in a 30 $cm^3/min$ flow of nitrogen as carrier gas.

Reaction products from the product flow out of the reactor were injected automatically into an on-line Agilent gas chromatograph with an FID detector an analyzed in-situ.

The results from the molecular sieve described in Example 1 are summarized in Table 8.

TABLE 8

| Time on Stream, h | 0.50 | 0.86 | 1.21 | 1.57 | 1.93 | 2.29 | 2.65 | 3.01 |
|---|---|---|---|---|---|---|---|---|
| Conversion, wt. % | 100 | 100 | 100 | 99.9 | 100 | 99.8 | 100 | 100 |
| Selectivity to Ethylene and Propylene, wt. % | 52.7 | 59.3 | 64.0 | 66.9 | 69.4 | 71.4 | 71.9 | 72.3 |
| Ethylene/Propylene Mole Ratio | 1.5 | 1.6 | 1.8 | 1.9 | 2.2 | 2.4 | 2.6 | 2.9 |
| Selectivity to Ethylene, wt. % | 26.6 | 31.0 | 34.7 | 37.8 | 41.0 | 43.8 | 45.8 | 47.6 |
| Selectivity to Propylene, wt. % | 26.0 | 28.3 | 29.3 | 29.2 | 28.5 | 27.6 | 26.1 | 24.7 |
| Selectivity to Butanes and Butenes, wt. % | 15.7 | 14.6 | 13.5 | 13.5 | 11.3 | 10.3 | 9.8 | 9.5 |
| Selectivity to $C_1$-$C_3$ Paraffins, wt. % | 24.9 | 18.3 | 13.5 | 13.5 | 8.3 | 7.2 | 6.7 | 6.2 |
| Selectivity to $C_{5+}$ Paraffins and Olefins, wt. % | 6.8 | 7.7 | 9.0 | 9.0 | 11.0 | 11.2 | 11.6 | 12.0 |

The results from the molecular sieve described in Example 2 are summarized in Table 9.

TABLE 9

| Time on Stream, h | 0.50 | 0.86 | 1.22 | 1.58 | 1.94 | 2.30 | 2.65 | 3.01 |
|---|---|---|---|---|---|---|---|---|
| Conversion, wt. % | 100 | 100 | 100 | 99.9 | 99.9 | 99.9 | 99.9 | 99.1 |
| Selectivity to Ethylene and Propylene, wt. % | 59.8 | 63.1 | 67.7 | 71.2 | 71.7 | 72.7 | 73.0 | 72.7 |
| Ethylene/Propylene Mole Ratio | 1.7 | 1.8 | 2.0 | 2.3 | 2.5 | 2.7 | 3.1 | 3.5 |
| Selectivity to Ethylene, wt. % | 31.6 | 34.1 | 38.8 | 43.0 | 44.5 | 46.9 | 49.0 | 50.7 |
| Selectivity to Propylene, wt. % | 28.2 | 28.9 | 28.9 | 28.2 | 27.2 | 25.8 | 24.0 | 22.0 |
| Selectivity to Butanes and Butenes, wt. % | 14.7 | 14.1 | 12.5 | 10.8 | 10.2 | 9.6 | 9.5 | 9.6 |

TABLE 9-continued

| | | | | | | | | |
|---|---|---|---|---|---|---|---|---|
| Selectivity to $C_1$-$C_3$ Paraffins, wt. % | 17.8 | 13.5 | 9.5 | 7.5 | 6.6 | 6.0 | 5.8 | 5.5 |
| Selectivity to $C_{5+}$ Paraffins and Olefins, wt. % | 7.8 | 9.3 | 10.4 | 10.5 | 11.5 | 11.7 | 11.7 | 12.2 |

The products from each of these two samples shown in Tables 8 and are consistent with those for a small pore zeolite in terms of product shape-selectivity in the reaction of methanol being catalytically converted to olefins of mostly $C_2$-$C_4$ size. No aromatic products were observed.

As used herein, the term "comprising" means including elements or steps that are identified following that term, but any such elements or steps are not exhaustive, and an embodiment can include other elements or steps.

Unless otherwise specified, the recitation of a genus of elements, materials or other components, from which an individual component or mixture of components can be selected, is intended to include all possible sub-generic combinations of the listed components and mixtures thereof.

All documents cited in this application are herein incorporated by reference in their entirety to the extent such disclosure is not inconsistent with this text.

The invention claimed is:

1. In a process for separating gases using a membrane containing a molecular sieve, the improvement comprising using as the molecular sieve an aluminosilicate molecular sieve composition having a $SiO_2/Al_2O_3$ mole ratio of from 10 to 50 comprising at least one intergrown phase comprising an ERI framework type molecular sieve and an LEV framework type molecular sieve.

2. A process for the production of light olefins from a feedstock comprising an oxygenate or mixture of oxygenates, the process comprising reacting the feedstock at effective conditions over a catalyst comprising an aluminosilicate molecular sieve composition having a $SiO_2/Al_2O_3$ mole ratio of from 10 to 50 comprising at least one intergrown phase comprising an ERI framework type molecular sieve and an LEV framework type molecular sieve.

3. The process of claim 2, wherein the light olefins are ethylene, propylene, butylene, or mixtures thereof.

4. The process of claim 2, wherein the oxygenate is methanol, dimethyl ether, or a mixture thereof.

5. A process for producing methylamine or dimethylamine comprising reacting methanol, dimethyl ether, or a mixture thereof, and ammonia in the gaseous phase in the presence of a catalyst comprising an aluminosilicate molecular sieve composition having a $SiO_2/Al_2O_3$ mole ratio of from 10 to 50 comprising at least one intergrown phase comprising an ERI framework type molecular sieve and an LEV framework type molecular sieve.

6. The process of claim 5, wherein the methanol, dimethyl ether, or mixture thereof, and ammonia are present in amounts sufficient to provide a carbon/nitrogen ratio of from 0.2 to 1.5.

7. The process of claim 5, conducted at a temperature of from 250° C. to 450° C.

8. A process for the reduction of oxides of nitrogen contained in a gas stream, wherein the process comprises contacting the gas stream with an aluminosilicate molecular sieve composition having a $SiO_2/Al_2O_3$ mole ration of from 10 to 50 comprising at least one intergrown phase comprising an ERI framework type molecular sieve and an LEV framework type molecular sieve.

9. The process of claim 8, conducted in the presence of oxygen.

10. The process of claim 8, wherein the molecular sieve composition contains one or more metals selected from the group consisting of Cr, Mn, Re, Mo, Fe, Ru, Co, Rh, Ir, Ni, Pd, Pt, Cu, Ag, Zn, Ga, In, Sn, and mixtures thereof.

11. The process of claim 10, wherein the metal is present in an amount of from 0.01 to 6 wt. %, based on the total weight of the molecular sieve composition.

12. The process of claim 8, wherein the gas stream is the exhaust stream of an internal combustion engine.

13. A process for treating exhaust gas that comprises a hydrocarbon combustion product, the method comprising:
    (a) contacting the exhaust gas with a molecular sieve composition for a period of time effective to facilitate adsorption of the hydrocarbon combustion product by the molecular sieve;
    (b) passing a purge gas through the molecular sieve composition to remove adsorbed hydrocarbon combustion product therefrom; and
    (c) contacting the purge gas containing the removed hydrocarbon combustion product with a hydrocarbon conversion catalyst;
wherein the molecular sieve composition is an aluminosilicate molecular sieve composition having a $SiO_2/Al_2O_3$ mole ratio of from 10 to 50 comprising at least one intergrown phase comprising an ERI framework type molecular sieve and an LEV framework type molecular sieve.

14. The process of claim 13, wherein the exhaust gas contains a plurality of hydrocarbon combustion products.

15. The process of claim 13, wherein the hydrocarbon combustion product is derived from the combustion of hydrocarbon fuel in an engine.

* * * * *